US00PP33665P2

(12) United States Plant Patent
Hansen

(10) Patent No.: US PP33,665 P2
(45) Date of Patent: Nov. 23, 2021

(54) ***BUDDLEIA* PLANT NAMED 'PRINCESS PINK'**

(50) Latin Name: *Buddleia davidii*
Varietal Denomination: Princess Pink

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/300,042

(22) Filed: Feb. 23, 2021

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242

CPC ... A01H 5/02; A01H 5/00; A01H 6/00; A01H 6/14; A01H 6/30
See application file for complete search history.

(56) References Cited

PUBLICATIONS

Hardy Plugs SWI-50 retrieved on May 4, 2021, retrieved from the Internet at http://hardyplugs.com/SWI-50.htm, 2 pp. (Year: 2020).*

* cited by examiner

*Primary Examiner* — June Hwu

(57) ABSTRACT

The new and distinct plant of *Buddleia* 'Princess Pink' is a rounded-mounded, multi-stemmed, winter-hardy butterfly bush with very long, mostly horizontal, thyrse producing sweetly fragrant flowers over a long season beginning mid-summer. Flowers have large petals of purplish-pink that are attractively offset by dark green foliage with silvery undersides. The new plant is valuable for attracting butterflies in the garden, landscaping en masse, as an accent or as a potted specimen.

1 Drawing Sheet

Botanical classification: *Buddleia davidii.*
Variety denomination: 'Princess Pink'.

STATEMENT REGARDING PRIOR DISCLOSURES UNDER 37 CFR 1.77(b)(6)

The first non-enabling disclosure of the claimed plant, in the form of a photograph and brief description was on a website operated by Walters Gardens, Inc. on Feb. 1, 2020. *Buddleia* 'Princess Pink' was listed with a photograph and brief description in the "Walters Gardens 20-21 Catalog" distributed initially on May 20, 2020. The claimed plant was first sold on Jul. 23, 2020 by Walters Gardens, Inc., who obtained the plant and all information relating thereto, from the inventor. No plants of *Buddleia* 'Princess Pink' have been sold in this country or anywhere in the world, nor has any disclosure of the new plant been made, more than one year prior to the filing date of this application, and such sale or disclosure within one year was either derived directly or indirectly from the inventor.

BACKGROUND OF THE PLANT

The present invention relates to the new and distinct butterfly bush plant of the Scrophulariaceae family, *Buddleia* 'Princess Pink' developed by the inventor on Aug. 15, 2015 as a single seedling selection from a self-pollination of the unreleased proprietary hybrid 14-38-6 (not patented) as the female or seed parent and male or pollen parent at a wholesale perennial nursery in Zeeland, Mich., USA. The new plant, was assigned the breeder code 15-57-103 through the evaluation trials. The new cultivar was discovered and selected as single individual flowering plant within the progeny of the above stated controlled self-pollination.

No plants of *Buddleia* 'Princess Pink' have been sold, under this or any other name, in this country or anywhere in the world, prior to the filing of this application, nor has any disclosure of the new plant been made prior to the filing of this application with the exception of that which may have been sold or disclosed within one year of the filing date of this application and was either derived directly or indirectly from the inventor.

*Buddleia* 'Princess Pink' was first asexually propagated from a single select plant in 2016 by stem cuttings at the same nursery in Zeeland, Mich. The resultant asexually propagated plants have been found to be stable and true to type in successive generations of asexual reproduction.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

In comparison to the new plant the female parent has lavender flowers that are more upright and the plant habit is more arching.

The nearest comparison plants known to the inventor are *Buddleia* 'Prince Charming' U.S. Plant Pat. No. 28,903, 'Pink Cascade' U.S. Plant Pat. No. 30,711, 'Pink Micro Chip' U.S. Plant Pat. No. 26,547, 'Pink Delight'(not patented) and 'Attraction' (not patented).

'Prince Charming' has a more compact habit and the thyrse are shorter and more upright, and the flowers are more cerise-pink. 'Pink Cascade' has a longer and more drooping thyrse, and the flower petal color is a medium pink. 'Pink Micro Chip' has a much smaller habit, the flowers are sterile and do not produce stamens, and the flower color is more reddish-purple. 'Pink Delight' has a much larger habit, the thyrse are more upright and not as dense with flowers, and the flower color is a slightly different hue. 'Pink Attraction' has a taller habit and a more mauve-pink flower color.

The proprietary hybrid 14-38-6 parent was not maintained as a plant or in photography, so no further comparison is possible.

*Buddleia* 'Princess Pink' is a unique winter-hardy butterfly bush different from all other *Buddleia* cultivars known to the inventor based on the following combined repeatedly observed distinguishing traits:

1. Winter-hardy butterfly bush shrub, with multiple-stemmed, well-branched, round, mounded habit;
2. Large, broad, many-flowered, elongated and mostly horizontal thyrse flowering over a prolonged season beginning mid-summer;
3. Flowers with apple-blossom pink petals;
4. Lanceolate foliage of dark green with silvery undersides.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
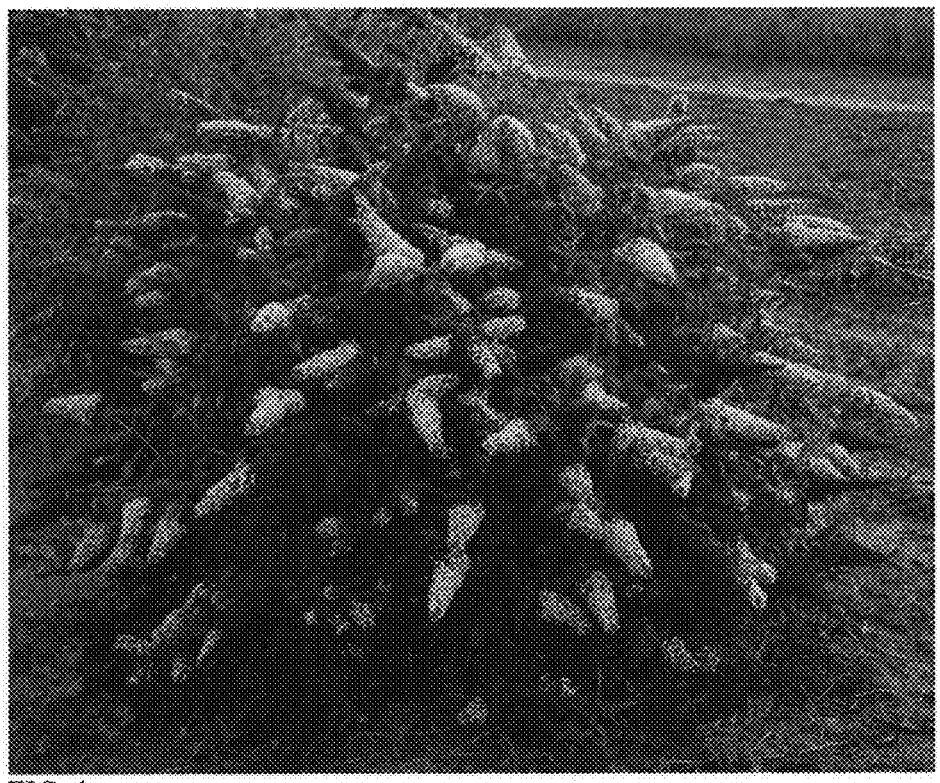
FIG. 1 shows the habit of a three-year-old plant in mid-season flowering.
Figure 2:
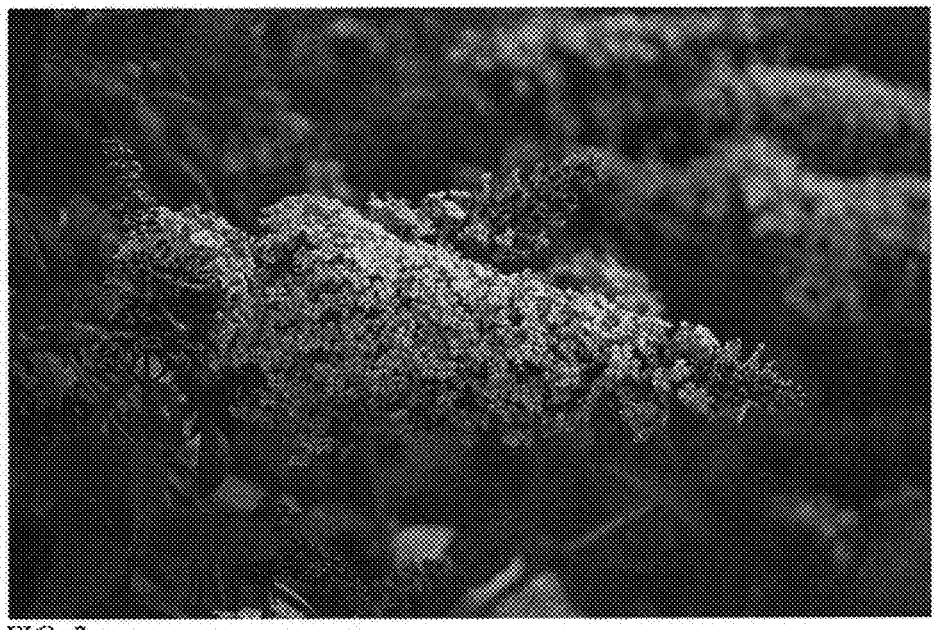
FIG. 2 shows a close-up of the inflorescence.

The following descriptions and color references are based on the 2015 edition of The Royal Horticultural Society Colour Chart except where common dictionary terms are used. The new plant, *Buddleia* 'Princess Pink', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in early spring.

Parentage: Unreleased proprietary hybrid 14-38-6 (not patented) as the female or seed patent and the male or pollen parent;

Propagation:

*Method*.—Softwood shoot cuttings.

*Time to initiate roots from tissue culture*.—About two weeks.

*Rooting habit*.—Normal, dense and branching, developing thick at base to about 1.5 cm diameter.

*Root color*.—Creamy white between RHS 159A and lighter than RHS 159 D depending on soil type.

*Crop time*.—Under normal summer growing conditions 12 to 15 weeks to flower in a four-liter container from cutting. Plant vigor is very good.

Plant description:

*Plant shape and habit*.—Winter-hardy, herbaceous to semi-woody, well-branched shrub with about 5 thick upright and branched main stems producing a rounded mound, to about 110 cm tall and about 150 cm wide.

*Stem*.—Terete and woody in lower portion, with exfoliating bark; younger distal portion tomentose to tomentulose; strong, mostly horizontal inflorescent with flower and bud production; average about 108 cm tall from soil line to just below terminal flowers, and about 30.0 mm diameter at the base; about five stems per plant, about 12 branches per main stem before distal flowers in upper 10 nodes, extending at about 45° angle from main stem.

*Stem color*.—Young distal portion just below flowers between RHS 146B and RHS 146C; basal 15 cm between RHS 200C and RHS 165B with striations between RHS 200A and RHS N199B.

*Internode*.—About 22 nodes per main stem below terminal thyrse, average internode length about 6.5 cm on unpinched plant, shorter proximally and longer distally.

Foliage description: Opposite; lanceolate; decussate; serrate to serrulate margin with about five teeth per cm, teeth about 1.0 mm long and 2.0 mm wide; young expanding leaves puberulent abaxial and adaxial, becoming glabrous adaxial; attenuate base and narrowly acute apex; sessile; moderate bulging between veins; no foliar fragrance detected;

*Leaf blade size*.—Up to about 10.0 cm long and about 2.8 cm wide, average about 7.0 cm long and about 2.2 cm wide; becoming smaller in distal portion of stem.

*Foliage color*.—Young expanding leaf adaxial nearest RHS 138A, young expanding abaxial nearest RHS 191B; mature leaves adaxial RHS NN137A, mature abaxial nearest RHS 191D.

*Veins*.—Reticulate; adaxial glabrous, slightly impressed; abaxial costate, puberulent.

*Vein color*.—Abaxial midrib between RHS 146D and RHS 145A and secondary veins nearest RHS NN137A; adaxial midrib between RHS 145D and RHS 145C and secondary veins nearest RHS 146A.

*Petioles*.—Leaves sessile.

*Inflorescence*.—Densely-flowered, conical, glomerate thyrse consisting of about 2,000 to 4,000 self-cleaning salverform flowers; main center thyrse to about 28.0 cm long and about 8.0 cm across, average about 24.0 cm long and 7.0 cm across; irregularly branched, sub-opposite, with up to about 50 branches, average 40 branches per thyrse; branches to about 6.5 cm long and 5.5 cm wide with up to 280 flowers per branch; beginning in mid-July and continuing until frost in Michigan.

*Inflorescence attitude*.—Slightly drooping, arching downwardly.

*Flower buds*.—Clavate with long tube base, apex rounded; one day prior to opening about 13.0 mm long, about 2.0 mm diameter in club, tube about 1.0 mm diameter and about 9.5 mm long.

*Flower bud color*.—Nearest RHS 72C in club portion, basal one-third of tube portion nearest RHS NN155B, distal two-thirds of tube nearest RHS 181B.

*Sepals*.—Typically four, proximal two-thirds connate, adpressed to corolla tube; acute apex; glabrous adaxial and pubescent abaxial; margin entire; fused in about the basal 1.5 mm and split in about the terminal 1.0 mm; forming a corolla about 2.5 mm long and about 1.0 mm across; individually less than about 1.0 mm wide at point of fusion.

*Sepal color*.—Adaxial and abaxial both variable, nearest RHS 138A and nearest RHS 187A in more sun.

*Flowers*.—Salverform; with straight terete tube about 10.0 mm long and 1.0 mm diameter, and a abruptly applanate face about 9.0 mm across; attitude outward from thyrse center; with corolla lobes perpendicular to corolla tube.

*Flowers fragrance*.—Pleasantly and distinctly sweet.

*Petals*.—Typically four; glabrous abaxial and on adaxial blades and tube, puberulent center adaxial tube about 4.0 mm long between face and base of anthers; blade rounded with crenulate margin; apex rounded; blade to about 3.5 mm across and about 4.0 mm long from fused face; corolla lobes free and not imbricate.

*Petal color*.—Adaxial face nearest RHS N74C upon opening, when fully open for at least a day and before dehiscing nearest RHS N74D; abaxial face when opening nearest RHS N74C, when fully open for at least a day and before dehiscing nearest RHS 73D; adaxial tube upon opening nearest N172B near face, base nearest RHS 145D and center nearest 172B, when fully open for at least a day until just before dropping base nearest RHS 155A, near face nearest RHS 25A and center portion nearest RHS N167B; abaxial tube upon opening base nearest RHS 145B, center portion nearest RHS 185D and near face nearest RHS 182A, when fully open for at least a day until just prior dehiscing base nearest RHS NN155C, center portion and distally between RHS 179B and RHS 179C.

*Gynoecium*.—Pistil: single; about 5.0 mm long. Style: short, round, glabrous; about 1.8 mm long and about 0.2 mm diameter; color nearest RHS 145D. Stigma: oblong ellipsoidal with acute apex; minutely puberulent; about 0.5 mm in diameter and about 1.3 mm long; color nearest RHS 145B. Ovary: superior; ellipsoidal with rounded apex and rounded base; about 0.7 mm across and 1.8 mm tall; color nearest RHS 145A.

*Androecium*.—Typically four. Filaments: adnate to inner corolla tube for 6.0 mm; about 0.2 mm diameter; color variable between RHS NN155C at base and center portion and distally between RHS 179B and RHS 179C. Anthers: typically four; oblong; introrse; basifixed; longitudinal; about 1.2 mm long and 0.5 mm wide; color nearest RHS 18D. Pollen: globose, less than 0.1 mm long; color nearest RHS 158A.

*Pedicel*.—Short, puberulent, cylindrical; about 1.0 mm long and about 0.5 mm diameter; color nearest RHS 187A.

*Peduncle*.—Quadrangular in lower portion and more cylindrical in distal-most branching; puberulent; flexible and strong; to about 56.0 cm long total, and about 3.0 mm across at base below flowers.

*Peduncle color*.—Proximally nearest RHS 146D, distally becoming variable between RHS 187A and RHS 146C.

*Fruit*.—Moderate fruit set; oblong with acute apex; glabrous, bi-valved, septicidal capsule; about 6.0 mm long and about 2.0 mm diameter.

*Fruit color*.—As maturing nearest RHS 138B when mature and dehiscing between RHS N199C and RHS 165B.

*Seed*.—Elongated ellipse with sharply acute ends; about 3.0 mm long and about 0.1 mm diameter in center.

*Seed color*.—In center RHS N199B, ends between RHS 199D and RHS 161D.

Disease resistance: The new plant is not susceptible to deer browsing. Other pest and disease resistance beyond that common to butterfly bush cultivars has not been observed. The plant grows best with plenty of moisture and adequate drainage, but is able to tolerate some drought when mature.

Hardiness at least from USDA zone 6 through 10, crown and root hardy to at least zone 5b.

It is claimed:

1. A new cultivar of winter-hardy butterfly bush plant named *Buddleia* 'Princess Pink' as herein illustrated and described.

* * * * *